(12) United States Patent
Silverman et al.

(10) Patent No.: US 8,969,413 B2
(45) Date of Patent: Mar. 3, 2015

(54) METHODS OF USING (1S,3S)-3-AMINO-4-DIFLUORO METHYLENYL-1-CYCLOPENTANOIC ACID

(75) Inventors: Richard B. Silverman, Northbrook, IL (US); Stephen L. Dewey, Manorville, NY (US); Steven Miller, Corona, CA (US)

(73) Assignees: Catalyst Pharmaceutical Partners, Coral Gables, FL (US); Brookhaven Science Associates, Upton, NY (US); Northwestern University, Evanston, IL (US)

( * ) Notice: Subject to any disclaimer, the term of this patent is extended or adjusted under 35 U.S.C. 154(b) by 0 days.

(21) Appl. No.: 13/581,187

(22) PCT Filed: Feb. 25, 2011

(86) PCT No.: PCT/US2011/026309
§ 371 (c)(1),
(2), (4) Date: Nov. 5, 2012

(87) PCT Pub. No.: WO2011/106692
PCT Pub. Date: Sep. 1, 2011

(65) Prior Publication Data
US 2013/0041028 A1 Feb. 14, 2013

Related U.S. Application Data

(60) Provisional application No. 61/308,030, filed on Feb. 25, 2010.

(51) Int. Cl.
*A01N 37/30* (2006.01)
*A61K 31/205* (2006.01)
*A61K 31/195* (2006.01)
*A61K 31/197* (2006.01)

(52) U.S. Cl.
CPC ............ *A61K 31/195* (2013.01); *A61K 31/197* (2013.01)
USPC ........................................... 514/556

(58) Field of Classification Search
None
See application file for complete search history.

(56) References Cited

U.S. PATENT DOCUMENTS

| | | | | |
|---|---|---|---|---|
| 6,462,084 B1 * | 10/2002 | Dewey et al. | ................. | 514/561 |
| 6,794,413 B1 * | 9/2004 | Silverman et al. | ............ | 514/573 |
| 6,906,099 B2 * | 6/2005 | Dewey et al. | ................. | 514/454 |
| 7,381,748 B1 * | 6/2008 | Silverman et al. | ............ | 514/573 |

* cited by examiner

*Primary Examiner* — Dennis Heyer
*Assistant Examiner* — Daniel M Podgorski
(74) *Attorney, Agent, or Firm* — Keller Life Science Law, P.A.; Michael J. Keller (57) ABSTRACT

(1S,3S)-3-amino-4-difluoromethylenyl-1-cyclopentanoic acid also known as CPP-115 or its pharmaceutically acceptable salts can be used to treat addiction and neurological disorders such as epilepsy without side effects such as visual field defects caused by vigabatrin (Sabril).

21 Claims, 5 Drawing Sheets

METHODS OF USING (1S,3S)-3-AMINO-4-DIFLUORO METHYLENYL-1-CYCLOPENTANOIC ACID

This application is a continuation-in-part of PCT application US/11/26309 filed on Feb. 25, 20011 which claims priority to U.S. provisional application No. 61/308,030 filed on Feb. 25, 2010, the contents of which are expressly incorporated by reference. All references cited herein are expressly incorporated by reference.

GOVERNMENT SUPPORT

This invention was made with government support under GM066132 awarded by the National Institutes of Health and DE-AC02-98CH10886 awarded by the Department of Energy. The government has certain rights in the invention.

Vigabatrin (γ-vinyl GABA) is sold worldwide under the trademark Sabril for treatment of epilepsy and has been studied for treatment of drug addiction. Vigabatrin's well known mechanism of action is the irreversible inhibition of gamma-aminobutyric acid-aminotransferase (GABA-AT). This enzyme is responsible for the catabolism of gamma aminobutyric acid (GABA) in the brain. Inhibition of this enzyme results in an elevation of brain levels of GABA. The elevation of brain GABA (the brain's primary inhibitory neurotransmitter) results in a decrease of neuron excitability and as such reduces uncontrolled firing of neurons, which leads to a reduction in epileptic seizures.

Unfortunately, long term use of the drug results in a constriction of the patient's visual field which in turn has prevented vigabatrin from gaining widespread usage. Visual field defects were detectable in some patients in less than 2 months after initiation of therapy and was most pronounced at about 1 year. One third or more of patients were affected with visual field defects after multiple years of therapy with vigabatrin. In the United States, the Food and Drug Administration deemed Vigabatrin unapprovable in 1998 as a direct result of the visual field defects following agency conclusions that "FDA unaware of way to reliably prevent damage" and "FDA unable to propose sound monitoring plan" to identify damage. Vigabatrin was subsequently approved for treatment of spasms in infants and epileptic seizures in 2009. The FDA's press release on the approval stated:

"Damage to vision is an important safety concern with the use of Sabril. The drug will have a boxed warning to alert health care professionals to this risk of a progressive loss of peripheral vision with potential decrease in visual acuity. The risk of vision damage may increase based on the dosage and duration of use, but even the lowest doses of Sabril can cause vision damage. Periodic vision testing is required for those taking Sabril. Because of the risk of permanent vision damage, the drug will be available only through a restricted distribution program."

As launched Sabril contains a black boxed warning as follows:

| WARNING: VISION LOSS |
|---|
| See full prescribing information for complete boxed warning |
| SABRIL causes progressive and permanent bilateral concentric visual field constriction in a high percentage of patients. In some cases, SABRIL may also reduce visual acuity. |
| Risk increases with total dose and duration of use, but no exposure to SABRIL is known that is free of risk of vision loss |
| Risk of new and worsening vision loss continues as long as SABRIL is used, and possibly after discontinuing SABRIL |

| WARNING: VISION LOSS |
|---|
| See full prescribing information for complete boxed warning |
| Periodic vision testing is required for patients on SABRIL, but cannot reliably prevent vision damage |
| Because of the risk of permanent vision loss, SABRIL is available only through a special restricted distribution program |

U.S. Pat. No. 6,713,497 teaches that vitamin B6 may be used to mitigate visual field defects caused by vigabatrin. Taurine deficiency is also known in the art as a possible contributing factor to the visual field defects resulting from vigabatrin administration. Jammoul, et al., Taurine Deficiency is a Cause of Vigabatrin Induced Retinal Phototoxicity, Ann. Neurol 2009: 65:98-107. Addit A need exists in the art to treat patients with GABA aminotransferase inhibitors without the side effects of vigabatrin.

U.S. Pat. Nos. 7,381,748 and 6,794,413, which are incorporated herein by reference disclose the compound (1S,3S)-3-amino-4-difluoromethylenyl-1-cyclopentanoic acid. The literature has shown that (1S,3S)-3-amino-4-difluoromethylenyl-1-cyclopentanoic acid is approximately 186 times more potent as a mechanism-based inactivator of γ-aminobutyric acid aminotransferase (GABA-AT) than the anticonvulsant drug and GABA-AT inactivator vigabatrin (1, Sabril™) under nonoptimal conditions (Pan, Y.; Qiu, J.; Silverman, R. B. Design, Synthesis, and Biological Activity of a Difluoro-substituted, Conformationally-rigid Vigabatrin Analogue As a Potent γ-Aminobutyric Acid Aminotransferase Inhibitor. *J. Med. Chem.* 2003, 46, 5292-5293).

It has been surprisingly discovered that (1S,3S)-3-amino-4-difluoromethylenyl-1-cyclopentanoic acid does not inhibit [$^3$H]GABA uptake in neurons, astrocytes, or mammalian cells recombinantly expressing the four different human GABA transporter subtypes (hGAT-1, hBGT-1, hGAT-2, and hGAT-3), nor does it bind to $GABA_A$ or $GABA_B$ receptors in rat brain homogenate, or affect $GABA_C$ receptor activity in *Xenopus laevis* oocytes. Thus, it appears that (1S,3S)-3-amino-4-difluoromethylenyl-1-cyclopentanoic acid is selective for GABA-AT.

U.S. Pat. Nos. 6,906,099; 6,890,951; 6,828,349; 6,593,367; 6,541,520; 6,395,783; 6,323,239; and 6,057,368, describe and/or claim the use of vigabatrin in the treatment of addiction from cocaine, nicotine, methamphetamine, morphine, heroin, ethanol, phencyclidine, methylenedioxymethamphetamine, and/or PCT. The contents of such patents are expressly incorporated herein by reference.

U.S. Pat. No. 6,462,084 describes and/or claims the use of vigabatrin in the treatment of obsessive compulsive disorders including general anxiety disorder, pathological or compulsive gambling disorder, compulsive eating (obesity), body dysmorphic disorder, hypochondriasis, pathologic grooming conditions, kleptomania, pyromania, attention deficit hyperactivity disorder and impulse control disorders. The contents of U.S. Pat. No. 6,462,084 is expressly incorporated herein by reference.

U.S. Pat. No. 6,939,876 describes and/or claims the use of vigabatrin in the treatment to prevent addiction to opioid analgesics by co administration of vigabatrin. The contents of U.S. Pat. No. 6,939,876 is expressly incorporated herein by reference.

Gabaergic drugs are those that improve secretion or transmission of GABA. These drugs as a family have been used to treat a wide variety of nervous system disorders including fibromyalgia, neuropathy, migraines related to epilepsy, restless leg syndrome, and post traumatic distress disorder.

Gabaergic drugs include $GABA_A$ and $GABA_B$ receptor ligands, GABA reuptake inhibitors, GABA aminotransferase inhibitors, GABA analogs, or molecules containing GABA itself. Preferred GABAergic drugs include valproate and its derivatives, vigabatrin, pregabalin, gabapentin and tiagabine.

As reported in the literature, although vigabatrin is an irreversible inhibitor of GABA-AT, its binding to GABA-AT is relatively weak ($K_I$=3.2 mM, $k_{inact}$=0.37, $k_{inact}/K_I$=0.11)[1] Pan, Yue; Qiu, Jian; Silverman, Richard B.; "Design, Synthesis, and biological Activity of a Difluoro-Substituted, Conformationally rigid Vigabatrin Analogue as a Potent γ-Aminobutyric Acid Aminotransferase Inhibitor", J. Med. Chem., 2003, 46(25), 5292-5293. Dr. Richard Silverman elucidated the mechanism by which vigabatrin inactivates GABA-AT. Burke, James R.; Silverman, Richard B.; "Mechanism of inactivation of γ-aminobutyric acid aminotransferase by the antiepilepsy drug γ-vinyl GABA (vigabatrin)", J. Am. Chem. Soc., 1991, 113(24), 9341-9349 and then set out to develop a new GABA-AT inhibitor that would exhibit superior binding and enzyme inactivation when compared to vigabatrin. The development work ultimately culminated in the development of (1S,3S)-3-amino-4-difluoromethylenyl-1-cyclopentanoic acid (U.S. Pat. Nos. 6,794,413 and 7,381,748, referred to as compound 2 in the text below). The contents of U.S. Pat. Nos. 6,794,413 and 7,381,748 are expressly incorporated herein by reference. During this development process, several other candidate compounds were created, including (1R,4S)-4-amino-cyclopent-2-ene-1-carboxylic acid (compound (1R,4S)-(+)-3 in reference 3 and referred to as compound 1 in the text below) and (1S,3S)-3-amino-4-methylenyl-1-cyclopentanoic acid (compound 6 in reference 1). As published in 2003, Silverman, et. al. (Pan, Yue; Qiu, Jian; Silverman, Richard B.; "Design, Synthesis, and biological Activity of a Difluoro-Substituted, Conformationally rigid Vigabatrin Analogue as a Potent γ-Aminobutyric Acid Aminotransferase Inhibitor", J. Med. Chem., 2003, 46(25), 5292-5293) stated that compound 1 "was not a GABA-AT inactivator but was a very good substrate with a specificity constant almost five times greater than that of GABA." It was further implied that compound 1's failure to inhibit GABA-AT made it a poor candidate for further development as an antiepileptic medication and work proceeded on a new candidate molecule. A later candidate molecule was compound 6 in reference 1. As published in Silverman 2003, "inactivation of GABA-AT was observed with 6, but when 2-mercaptoethanol was added to the incubation mixture, no inactivation occurred." The same publication goes on to explain that the lack of activity in the presence of 2-mercaptoethanol is an indication that the GABA-AT first acts on compound 6 to form an alpha-beta unsaturated ketone (3-oxo-4-methylenyl-1-cyclopentanoic acid, compound 8 in that publication). The mercaptoethanol then reacts with the alpha-beta unsaturated ketone before it can inactivate the enzyme. This is undesirable because it indicates that the reactive intermediate escapes the enzyme. To correct this deficiency, compound 6 was synthesized, which inactivated GABA-AT, even in the presence of 2-mercaptoethanol, so it was a true mechanism-based inactivator, and the reactive intermediate does not escape the enzyme prior to inactivation.

Once GABA-AT has been inactivated, it takes a number of days for the brain to synthesize new GABA-AT to replace the inactivated enzyme. Information Petroff, Ognen A. C.; Rothman, Douglas L.; "Measuring Human Brain GABA In Vivo, Effects of GABA-Transaminase Inhibition with Vigabatrin", Molecular Neurobiology, 1998, 16(1), 97-121 demonstrated that brain GABA levels remain substantially elevated for several days after administration of a single dose of vigabatrin. This observation is consistent with the theory that it takes several days for the brain to restore the GABA-AT activity.

Gabaergic drugs are also useful in treating Huntington's chorea ((a) Perry, T. L.; Hansen, S.; Lesk, D.; Kloster, M. "Amino Acids in Plasma, Cerebrospinal Fluid, and Brain of Patients with Huntington's Chorea." Adv. Neurol. 1972, 1, 609. (b) McGeer, P. L.; McGeer, E. G. "The GABA System and Function of the Basal Ganglia: Huntington's Disease." In GABA in Nervous System Function Roberts, E.; Chase, T. N.; and Tower, D. B.; Eds.; Raven Press: New York, 1976; pp. 487-495. (a) Butterworth, J.; Yates, C. M.; Simpson, J. "Phosphate-activated glutaminase in relation to Huntington's disease and agonal state." J. Neurochem. 1983, 41, 440. (b) Spokes, E. G. S. "Brain temperature after death." Adv. Exp. Med. Biol. 1978, 123, 461. (c) Wu, J. Y.; Bird, E. D.; Chen, M. S.; Huang, W. M. "Abnormalities of neurotransmitter enzymes in Huntington's chorea." Neurochem. Res. 1979, 4, 575. (d) Iversen, L. L.; Bird, E. D.; Mackay, A. V. P.; Rayner, C. N. "Analysis of glutamate decarboxylase in post-mortem brain tissue in Huntington's chorea." J. Psychiat. Res. 1974, 11, 255., Parkinson's disease Nishino, N.; Fujiwara, H.; Noguchi-Kuno, S.-A.; Tanaka, C. "GABA receptor but not muscarinic receptor density was decreased in the brain of patients with Parkinson's disease." Jpn. J. Pharmacol. 1988, 48, 331. Maker, H. S.; Weiss, C.; Weissbarth, S.; Silides, D. J.; Whetsell, W. "Regional activities of metabolic enzymes and glutamate decarboxylase in human brain." Ann. Neurol. 1981, 10, 377. (b) Rinne, U. K.; Laaksonen, H.; Riekkinen, P.; Sonninen, V. "Brain glutamic acid decarboxylase activity in Parkinson's disease." Eur. Neurol. 1974, 12, 13. (c) McGeer, P. L.; McGeer, E. G.; Wada, J. A.; Jung, E. "Effects of globus pallidus lesions and Parkinson's disease on brain glutamic acid decarboxylase." Brain Res. 1971, 32, 425., Alzheimer's disease (a) Aoyagi, T.; Wada, T.; Nagai, M.; Kojima, F.; Harada, S.; Takeuchi, T.; Takahashi, H.; Hirokawa, K.; Tsumita, T. "Increased g-aminobutyrate aminotransferase activity in brain of patients with Alzheimer's disease." Chem. Pharm. Bull. 1990, 38, 1748-1749. (b) Davies, P. "Neurotransmitter-related enzymes in senile dementia of the Alzheimer type." Brain Res. 1979, 171, 319. (c) Perry, E. K.; Gibson, P. H.; Blessed, G.; Perry, R. H.; Tomlinson, B. E. "Neurotransmitter enzyme abnormalities in senile dementia. Choline acetyltransferase and glutamic acid decarboxylase activities in necripsy brain tissue."J. Neurol. Sci. 1977, 34, 247. (d) Bowen, D. M.; White, P.; Flack, R. H. A.; Smith, C. B.; Davison, N. A. "Brain-decarboxylase activities as indices of pathological change in senile dementia." Lancet 1974, 1, 1247. (e) Kodama, K.; Kaitani, H.; Nanba, M.; Kondo, T.; Mikame, F.; Yoshida, H.; Sato, K.; Yanaihara, N. "Neurotransmitter analogs in body fluids of patients with dementia." Shinkei Kagaku 1981, 20, 496., and tardive dyskinesia Gunne, L. M.; Haeggstroem, J. E.; Sjoequist, B. "Association with persistent neuroleptic-induced dyskinesia of regional changes in brain GABA synthesis." Nature (London) 1984, 309, 347.

Published United States patent application number 20040023952 A1, Ser. No. 10/311,821, entitled Enhanced Brain Function by GABA-ergic Stimulation describes how gaba-ergic drugs are useful in treating variety of age-associated disorders of cortical decline in the elderly. These "age-associated" disorders of cortical decline extend on a continuum from normal age-related senescence to severe dementias associated with Alzheimer's disease and Parkinson's disease in an aging population. Published patent application 20040023952 A1 is expressly incorporated herein by reference.

Also unexpected is the fact that (1S,3S)-3-amino-4-difluoromethylenyl-1-cyclopentanoic acid has an activity more than 100 times that of vigabatrin in vitro. Using micropositron emission tomography imaging techniques, that (1S,3S)-3-amino-4-difluoromethylenyl-1-cyclopentanoic acid completely blocks cocaine-induced increases in synaptic dopamine in the nucleus accumbens as well as the expression of cocaine-induced conditioned place preference at a dose 100 times lower than that measured with vigabatrin.

Abbreviations: CPP, conditioned place preference; GABA, γ-aminobutyric acid; GABA-AT, γ-aminobutryic acid aminotransferase; μPET, micro-positron emission tomography; NAc, nucleus accumbens; VFD, visual field defect It is an object of the present invention to deliver a GABA aminotransferase inhibitor to a patient in need thereof while reducing visual field defects.

It is an object of this invention to treat patients using an irreversible inhibitor of GABA aminotransferase.

It is an object of the present invention to suppress dopamine levels below the level attainable by administration of vigabatrin.

It is an object of the present invention to treat cocaine addiction using low doses of a GABA aminotransferase inhibitor.

It is an object of the present invention to treat cocaine addiction using (1S,3S)-3-amino-4-difluoromethylenyl-1-cyclopentanoic acid or its pharmacologically acceptable salts.

DETAILED DESCRIPTION OF THE INVENTION

The content of all references cited herein is expressly incorporated by reference.

Vigabatrin is known in the literature and has been approved for use in treating epilepsy and seizures and has been studied for treatment of drug addiction. U.S. Pat. Nos. 6,906,099; 6,890,951; 6,828,349; 6,593,367; 6,541,520; 6,395,783; 6,323,239; and 6,057,368 which describe and/or claim the use of vigabatrin in the treatment of addiction from cocaine, nicotine, methamphetamine, morphine, heroin, ethanol, phencyclidine, methylenedioxymethamphetamine, and/or PCP. It is believed that compounds of the present invention will treat or prevent addiction of all of the following drugs: mu opioid receptor agonists including but not limited to, 3-methylfentanyl, 3-methylthiofentanyl, Acetorphine, Acetyl methadol, Acetyl-alpha-methylfentanyl, Acetylhydrocodone, Alfentanil, Allylprodine, Alphaacetylmethadol, Alphameprodine, Alphamethadol, Alpha-methylfentanyl, Alpha-methylthiofentanyl, Benzethidine, Benzylmorphine, Beta-hydroxy-3-methylfentanyl, Beta-hydroxyfentanyl, Betameprodine, Betamethadol, Betaprodine, Betascetylmethadol, Bezitramide, Buprenorphine, Butorphanol, Carfentanil, Codeine, Cyprenorphine, Desomorphine, Dextromoramide, Diampromide, Diethylthiambutene, Difenoxin, Dihydrocodeine, Dihydroetorphine, Dihydromorphine, Dimenoxadol, Dimepheptanol, Dimethylthiambutene, Dioxaphetyl butyrate, Diphenoxylate, Dipipanone, Drotebanol, Ethylmethylthiambutene, Ethylmorphine, Etonitazine, Etorphine, Etoxeridine, Fentanil, Fentanyl, Furethidine, Heroin (diacetyl morphine), Hydrocodone, Hydromorphinol, Hydromorphone, Hydroxypethidine, Isomethadone, Ketobemidone, LAAM (levoalphaacetylmethadol), Levomethorphan, Levomoramide, Levophenacylmorphan, Levorphanol, Meperidine, Metazocine, Methadone, Methyldesorphine, Methyldihydromorphine, Metopon, Morpheridine, Morphine, MPPP (1-methyl-4-phenyl-4-propionoxypiperidine), Myrophine, Nalorphine, Nepetalactone, Nicocodeine, Nicomorphine, Noracymethadol, Norlevorphanol, Normethadone, Normorphine, Norpipanone, Opium, Oripavine, Oxycodone, Oxymorphone, Para-fluorofentanyl, Pentazocine, PEPAP (1-(2-phenylethyl)-4-phenyl-acetoxypiperidine), Phenampromide, Phenazocine, Phenedoxone, Phenomorphan, Phenoperidine, Pholcodin, Piminodine, Piritramide, Proheptazine, Properidine, Propiram, Propxyphene, Racemethorphan, Racemoramide, Racemorphan, Remifentanil, Sufentanil, Tapentadol, Tapentadol, Thebaine, Thiofentanyl, Tilidine, Tramadol, Trimeperidine; dopamine reuptake inhibitors; CBI receptor agonists, alpha adrenergic receptor agonists, dopamine receptor agonists; dopamine reuptake inhibitors, GABA agonists, nicotinic receptor agonists. Addictive drugs to which the present invention is applicable can be readily identified from 21 C.F.R. §1308 Schedules of Controlled Substances, et seq, which is expressly incorporated by reference.

It is well established that the neurochemical response to cocaine and other drugs of abuse is characterized by a rapid elevation in the release of dopamine in the nucleus accumbens (NAc). Dewey, Stephen L.; Morgan, Alexander E.; Ashby, Charles R. Jr.; Horan Bryan; Kushner, Stephanie A.; Logan, Jean; Volkow, Nora D.; Fowler, Joanna S.; Gardner, Eliot L.; Brodie, Jonathan D.; A Novel Strategy for the Treatment of Cocaine Addiction. *Synapse* 1998, 30(2), 119-129 This increase in dopamine, and associated behaviors, can be antagonized by an increase in the concentration of γ-aminobutyric acid (GABA), which has been shown to occur with use of the epilepsy drug vigabatrin (1, Sabril™), a known mechanism-based inactivator. Silverman, R. B. *Mechanism-Based Enzyme Inactivation: Chemistry and Enzymology*, Vols. I and II; CRC Press; Boca Raton, Fla.; 1988. (b) Silverman, R. B. Mechanism-Based Enzyme Inactivators. *Methods Enzymol.* 1995, 249, 240-283 of γ-aminobutyric acid aminotransferase (GABA-AT). Lippert, B.; Metcalf, B. W.; Jung, M. J.; Casara, P.; 4-Aminohex-5-Enoic Acid, A Selective Catalytic Inhibitor of 4-Aminobutyric Aminotransferase In Mammalian Brain. *Eur. J. Biochem.* 1977, 74, 441-445. Vigabatrin is currently marketed for the treatment of infantile spasms (West's Syndrome) and refractory partial complex seizures in 65 countries, including the United States.

Vigabatrin also has been found to have utility in the treatment of stimulant addiction, (Karila, L.; Gorelick, D.; Weinstein, A.; Noble, F.; Benyamina, A.; Coscas, S.; Blecha, L.;

Lowenstein, W.; Martinot, J. L.; Reynaud, M.; Lepine, J. P. New treatments for cocaine dependence: a focused review. *Internat. J. Neuropsychopharmacol.* 2008, 11(3), 425-438. (b) Peng, X.-Q.; Li, X.; Gilbert, J. G.; Pak, A. C.; Ashby, C. R.; Brodie, J. D.; Dewey, S. L.; Gardner, E. L.; Xi, Z.-X. Gamma-vinyl GABA inhibits cocaine-triggered reinstatement of drug-seeking behavior in rats by a non-dopaminergic mechanism. *Drug Alcohol Depend.* 2008, 97(3), 216-225. Vigabatrin has been specifically shown to be effective in animal models for cocaine, (a) Perry, T. L.; Hansen, S.; Lesk, D.; Kloster, M. "Amino Acids in Plasma, Cerebrospinal Fluid, and Brain of Patients with Huntington's Chorea." *Adv. Neurol.* 1972, 1, 609. (b) McGeer, P. L.; McGeer, E. G. "The GABA System and Function of the Basal Ganglia: Huntington's Disease." In *GABA in Nervous System Function* Roberts, E.; Chase, T. N.; and Tower, D. B.; Eds.; Raven Press: New York, 1976; pp. 487-495) nicotine, (Dewey, Stephen L.; Brodie, Jonathan D.; Gersimov, Madina; Horan, Bryan; Gardner, Eliot L.; Ashby, Charles R. Jr.; A Pharmaceutical Strategy for the Treatment of Nicotine Addiction. *Synapse* 1999, 31(1), 76-86), methamphetamine, heroin, ethanol (Gersimov, Madina R.; Ashby, Charles R. Jr.; Gardner, Eliot L.; Mills, Mark J.; Brodie, Jonathan D.; Dewey, Stephen L.; Gamma-vinyl GABA Inhibits Methamphetamine, Heroin, or Ethanol-Induced Increases in Nucleus Accumbens Dopamine. *Synapse* 1999, 34(1), 11-19.), and combination addictions (Stromberg, Michael F.; Mackler, Scott A.; Volpicelli, Joseph R.; O'Brien, Charles P.; Dewey, Stephen L.; The effect of gamma-vinyl-GABA on the consumption of concurrently available oral cocaine and ethanol in the rat. *Pharmacol. Biochem. Behav.* 2001, 68, 291-299). Vigabatrin treatment also is effective for stimulant addiction in humans ((a) Brodie, Jonathan D.; Figueroa, Emilia; Dewey, Stephen L.; Treating Cocaine Addiction: From Preclinical to Clinical Trial Experience with γ-vinyl GABA. *Synapse* 2003, 50(3), 261-265. (b) Brodie, Jonathan D.; Figueroa, Emilia; Laska, Eugene M.; Dewey, Stephen L.; Safety and Efficacy of γ-Vinyl GABA (GVG) for the Treatment of Methamphetamine and/or Cocaine Addiction. *Synapse* 2005, 55(2), 122-125.), including a recently reported randomized, double-blind, placebo-controlled, trial of 103 subjects (Brodie, Jonathan D.; Case, Brady G.; Figueroa, Emilia; Dewey, Stephen L.; Robinson, James A.; Wanderling, Joseph A.; Laska, Eugene M.; Randomized, Double-Blind, Placebo-Controlled Trial of Vigabatrin for the Treatment of Cocaine Dependence in Mexican Parolees. *Am. J. Psychiatry* 2009, 166, 1269-12770, in which 28.0% of subjects treated with vigabatrin achieved abstinence compared to 7.5% of subjects treated with placebo.

The acceptance of vigabatrin for the treatment of both epilepsy and as a potential treatment for stimulant addiction has been hampered primarily by concerns about abnormalities of the peripheral visual field (visual field defects or visual field defect) in 25-50% of patients following chronic administration of vigabatrin. Willmore, L. James; Abelson, Mark B.; Ben-Menachem, Elinor; Pellock, John M.; Shields, Donald; Vigabatrin: 2008 Update. *Epilepsia* 2009, 50(2), 163-173; Wild, John M.; Chiron, Catherine; Ahn, Hyosook; Baulac, Michel; Bursztyn, Joseph; Gandolfo, Enrico; Goldberg, Ivan; Goni, Francisco Javier; Mercier, Florence; Nordmann, Jean-Philippe; Safran, Avinoam B.; Schiefer, Ulrich; Perucca, Emilio; Visual Field Loss in Patients with Refractory Partial Epilepsy Treated with Vigabatrin. *CNS Drugs* 2009, 23(11), 965-982 Shorter duration exposure in connection with studies of the treatment of stimulant addiction with vigabatrin does not show any occurrence of visual field defect, which corroborates the prevailing belief that the development of visual field defect results from prolonged exposure to vigabatrin. Fechtner, Robert D.; Khouri, Albert S.; Figueroa, Emilia; Ramirez, Marina; Federico, Martha; Dewey, Stephen L.; Brodie, Jonathan D.; Short-term Treatment of Cocaine and/or Methamphetamine Abuse with Vigabatrin-Ocular Safety Pilot Results. *Arch. Ophthalmol.* 2006, 124, 1257-1262 Treatment of addictive disorders is usually long term or chronic therapy. The long term administration of vigabatrin is known causes visual field defects. The mechanism leading to the visual field defect is not known, but it remains an active area of research. Visual field defects might occur from elevated GABA levels as a result of inactivation of GABA-AT, could be a direct toxic effect of vigabatrin, could be the consequence of an enzymatically produced byproduct from one of the enzyme inactivation mechanisms, or some combination of these potential mechanisms.

A new synthetic compound, (1S,3S)-3-amino-4-difluoromethylenyl-1-cyclopentanoic acid (2), was designed as a mechanism-based inactivator of GABA-AT, which could generate a more reactive intermediate along the pathway to attachment to the active site of GABA-AT via a Michael addition Pan, Y.; Qiu, J.; Silverman, R. B.; Design, Synthesis and biological Activity for a Difluoro-substituted, conformationally-rigid Vigabatrin Analogue As a Potent γ-Aminobutyric Acid Aminotransferase Inhibitor. *J. Med. Chem.* 2003, 46, 5292-5293. In contrast to the high $K_I$ value (3.2 mM[12]; 10 mM[3]) reported for vigabatrin as an inactivator of GABA-AT, the new synthetic GABA-AT inactivator (2) has a $K_I$ value of 31 μM[12]. A comparison of the $k_{inact}/K_I$ values (a measure of the efficiency of the inactivator) indicated that (1S,3S)-3-amino-4-difluoromethylenyl-1-cyclopentanoic acid is 186 times more effective as an inactivator of GABA-AT than vigabatrin under suboptimal conditions (at optimal conditions for substrate turnover, the rate of inactivation is too rapid to measure; these values were obtained at a pH and temperature well below the optimum). Despite irreversibility of the inhibition, the low potency of vigabatrin translates into treatment doses of 1-3 g/day (U.S. Labeling for Sabril® http://www.lundbeckinc.com/USA/products/CNS/Sabril/sabril_PI_CPS.pdf. Because (1S,3S)-3-amino-4-difluoromethylenyl-1-cyclopentanoic acid displayed superior enzyme inactivation properties compared to vigabatrin, we have carried out further pharmacological studies with (1S,3S)-3-amino-4-difluoromethylenyl-1-cyclopentanoic acid. The affinity of (1S,3S)-3-amino-4-difluoromethylenyl-1-cyclopentanoic acid at $GABA_A$ and $GABA_B$ receptors and its activity at the $GABA_C$ receptor as well as at four GABA transporter subtypes expressed either endogenously in neurons and astrocytes or recombinantly in mammalian cell lines was determined. Because of the preponderance of data indicating vigabatrin is effective for the treatment of addiction, the previously reported[11] lack of visual field defect observed for short vigabatrin exposure durations required for the treatment of stimulant addiction, and the relatively short duration of drug exposure needed for addiction treatment, the effect of (1S,3S)-3-amino-4-difluoromethylenyl-1-cyclopentanoic acid on cocaine-induced conditioned place preference in rats (an animal model for effectiveness of addiction treatments) also was investigated. Mechanistic similarities between vigabatrin and (1S,3S)-3-amino-4-difluoromethylenyl-1-cyclopentanoic acid for the treatment of addiction were also investigated by μPET imaging to measure the ability of (1S,3S)-3-amino-4-difluoromethylenyl-1-cyclopentanoic acid to antagonize cocaine-induced increases in synaptic nucleus accumbens dopamine.

While the compound (1S,3S)-3-amino-4-difluoromethylenyl-1-cyclopentanoic acid has been shown to be a GABA aminotransferase inhibitor like vigabatrin, surprisingly (1S,3S)-3-amino-4-difluoromethylenyl-1-cyclopentanoic acid does not inhibit the reuptake of GABA.

The phrase "pharmaceutically acceptable salt(s)", as used herein, means those salts of compounds of the invention that are safe and effective for use in mammals and that possess the desired biological activity. Pharmaceutically acceptable salts include salts of acidic or basic groups present in vigabatrin or (1S,3S)-3-amino-4-difluoromethylenyl-1-cyclopentanoic acid. Suitable acids include: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid), salicylic acid, sebacic acid, stearic acid, succinic acid, sulfuric acid, tartaric acid, thiocyanic acid, toluenesulfonic acid, undecylenic acid. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. (1S,3S)-3-amino-4-difluoromethylenyl-1-cyclopentanoic acid. can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 J. Pharm Sci 1-19 (1977) and P. Heinrich Stahl, Camille G. Wermuth (Eds.) *Handbook of Pharmaceutical Salts: Properties, Selection, and Use*, Wiley, (2002), the contents of which are expressly incorporated herein by reference. The administration of r (1S,3S)-3-amino-4-difluoromethylenyl-1-cyclopentanoic acid hydrochloride salt is expressly contemplated.

Materials

Vigabatrin, (R)-baclofen, GABA, isoguvacine, sodium pyruvate, theophylline, gentamycin, and all buffer reagents were purchased from Sigma-Aldrich (St. Louis, Mo., USA). (1S,3S)-3-Amino-4-difluoromethylenyl-1-cyclopentanoic acid (2) was synthesized as reported previously.[12] [$^3$H]GABA (35 or 40.0 Ci/mmol) and [$^3$H]muscimol (36.6 Ci/mmol) were purchased from PerkinElmer (Boston, Mass., USA). All reagents for cell culturing were purchased from Invitrogen (Paisley, UK). Cocaine USP was provided by the National Institute on Drug Abuse (NIDA). All animals were adult male Sprague-Dawley rats (200-225 g, supplied by Taconic Farms, Germantown, N.Y.).

GABA Uptake Assay

[$^3$H]GABA Uptake Assay at Human GABA Transporters tsA201 cells were cultured in GlutaMAX-I DMEM supplemented with 10% fetal bovine serum, penicillin (100 U/ml), and streptomycin (100 µg/ml) at 37° C. in a humidified atmosphere of 95% air and 5% $CO_2$. The plasmids encoding hGAT-1, hBGT-1, hGAT-2, and hGAT-3, (Kvist, T.; Christiansen, B.; Jensen, A. A.; Bräuner-Osborne, H. The four human gamma aminobutyric acid (GABA) transporters: pharmacological characterization and validation of a highly efficient screening assay. *Comb. Chem. High Throughput Screen* 2009, 12, 241-249) respectively, were transfected into tsA201 cells using PolyFect according to the protocol of the manufacturer (Qiagen, West Sussex, UK). The next day, the tsA201 cells transiently expressing each of the four human GABA transporter subtypes were split into poly-D-lysine-coated white 96-well plates (PerkinElmer). The pharmacological assays were performed 36-48 h after transfection exactly as described previously Christiansen, B.; Meinild, A. K.; Jensen, A. A,; Bräuner-Osborne, H. Cloning and characterization of a functional human gamma-aminobutyric acid (GABA) transporter, human GAT-2. *J. Biol. Chem.* 2007, 282, 19331-19341. In brief, assay buffer supplemented with 30 nM [$^3$H]GABA and test compounds was added to the cells, and the uptake of [$^3$H]GABA was determined after incubation at 37° C. for 3 min. Quantification was performed by using Microscint™ 20 scintillation fluid (PerkinElmer) and a Packard TopCount microplate scintillation counter.

[$^3$H]GABA Uptake Assay at Mouse GABA Transporters

Cortical astrocytes were cultured essentially as previously described. Hertz L, Juurlink B H J, Hertz E, Fosmark H and Schousboe A. Preparation of Primary Cultures of Mouse (Rat) Astrocytes, in A Dissection and Tissue Culture Manual of the Nervous System (Shahar A, de Vellis J, Vernadakis A and Haber B eds) pp 105-108, Alan R. Liss, Inc., New York, 1989 The neopallium was removed from new born NMRI mice (Taconic, Denmark) and passed through an 80 µm nylon sieve and cultured in modified Dulbecco's modified Eagle's medium with fetal calf serum. The calf serum was lowered from 20% to 10% over three weeks, and finally the astrocytes were allowed to differentiate using 0.25 mM dibutyryl cyclic AMP during the last week of growth.

Cortical neurons were cultured essentially as previously described by removing the neopallium of 15-day old NMRI embryos by dissection followed by mild trypsination. Hertz E, Yu A C H, Hertz L, Juurlink B H J and Schousboe A. Preparation of Primary Cultures of Mouse Cortical Neurons, in A Dissection and Tissue Culture Manual of the Nervous System (Shahar A, de Vellis J, Vernadakis A and Haber B eds) pp 183-186, Alan R. Liss, Inc., New York, 198. The neurons were cultured in 10% fetal calf serum and, after 48 h, cytosine arabinoside was added to a final concentration of 20 µM to prevent glial proliferation. Four cultures of stably transfected Human Embryonic Kidney (HEK)-293 cells expressing mGAT1-4 were prepared by the method previously reported. White H S, Sarup A, Bolvig T, Kristensen A S, Petersen G, Nelson N, Pickering D S, Larsson O M, Frølund B, Krogsgaard-Larsen P and Schousboe A. Correlation Between Anticonvulsant Activity and Inhibitory Action on Glial Gamma-Aminobutyric Acid Uptake of the Highly Selective Mouse Gamma-Aminobutyric Acid Transporter 1 Inhibitor 3-Hydroxy-4-Amino-4,5,6,7-Tetrahydro-1,2-Benzisoxazole and Its N-Alkylated Analogs. *J Pharmacol Exp Ther.* 2002, 302, 636-644 The stable cell lines are under the selection pressure of blasticidin-S at 5 µg/mL. Determinations of the $IC_{50}$ values were conducted as described earlier. Bolvig T, Larsson O M, Pickering D S, Nelson N, Falch E, Krogsgaard-Larsen P and Schousboe A. Action of Bicyclic Isoxazole GABA Analogues on GABA Transporters and Its Relation to Anticonvulsant Activity. *Eur. J. Pharmacol.* 1999, 375, 367-374 In brief, [$^3$H]GABA uptake was assessed at 37° C. for 3 min on desired cells in PBS buffer containing 1 µM GABA, 13 nM [$^3$H] GABA, and test compound. Radioactivity was measured using Microscint™ 20 scintillation fluid (PerkinElmer) and a Packard TopCount microplate scintillation counter.

GABA Receptor Binding Assays

Receptor Preparations

GABA$_A$ and GABA$_B$ binding assays were performed using rat brain synaptic membranes of cortex and the central hemispheres from adult male Sprague-Dawley rats with tissue preparation as earlier described. Ransom, R. W.; Stec, N. L. Cooperative modulation of [$^3$H]MK-801 binding to the N-methyl-D-aspartate receptor-ion channel complex by L-glutamate, glycine, and polyamines. *J. Neurochem.* 1988, 51, 830-836. On the day of the assay, the membrane preparation was quickly thawed, suspended in 40 volumes of ice-cold 50 mM Tris-HCl buffer (pH 7.4) using an UltraTurrax homogenizer and centrifuged at 48,000 g for 10 min at 4° C. This washing step was repeated four times. The final pellet was resuspended in incubation buffer and the binding assay carried out as detailed below.

GABA$_A$ Receptor Activity Assay

Rat brain synaptic membranes (100 µg protein/aliquot) prepared above in Tris-HCl buffer (50 mM, pH 7.4) were incubated with [$^3$H]muscimol (5 nM) and 100 µM of compound 2 at 0° C. for 60 min in a total volume of 250 µl. GABA (1 mM) was used to define non-specific binding. The binding reaction was terminated by rapid filtration through GF/B unifilters (PerkinElmer) using a 96-well Packard FilterMate cell harvester, followed by washing with 3×250 µl of ice-cold binding buffer, drying, and adding scintillation fluid, as described for the [$^3$H]GABA uptake assay.

GABA$_B$ Receptor Binding Assay

For [$^3$H]GABA binding to the GABA$_B$ receptors, rat brain synaptic membranes (200 µg protein/aliquot) were suspended in Tris-HCl buffer (50 mM+2.5 mM CaCl$_2$, pH 7.4) and incubated with [$^3$H]GABA (5 nM), isoguvacine (40 µM), and 100 µM of compound 2 at 25° C. for 45 min in 1 ml total volume. Isoguvacine serves to saturate GABA$_A$ receptors. Hill, D. R.; Bowery, N. G. $^3$H-baclofen and $^3$H-GABA bind to bicuculline-insensitive GABA$_B$ sites in rat brain. *Nature* 1981, 290, 149-152 Non-specific binding was determined using 100 µM (R)-baclofen. Binding was terminated by filtration through Whatman GF/C filters, using a Brandell M-48R Cell Harvester; filters were washed with 3×3 ml of ice-cold buffer, and filter-bound radioactivity was counted in a Packard Tricarb 2100 liquid scintillation analyzer using 3 ml of Opti-fluor scintillation fluid (PerkinElmer).

Electrophysiology

Expression of ρ1 in *Xenopus leavis* Oocytes

Human ρ1 cDNA encapsulated in pcDNA1.1 was linearized with Not1. Linearized cDNA was transcribed to mRNA using the T7 "mMESSAGE mMACHINE" kit (Ambion Inc. Austin, Tex., USA) as previously described. Chebib; M; Duke, R. K.; Allan, R. A.; Johnston, G. A. R. The effects of cyclopentane and cyclopentene analogs of GABA at recombinant GABA$_C$ receptors. *Eur. J. Pharmacol.* 2001, 430, 185-192. GABA$_C$ receptor activity assays were performed in oocytes harvested from *Xenopus laevis* (housed in the Department of Veterinary Science at the University of Sydney) and defolliculated. The oocytes were stored in ND96 solution (in mM) NaCl (96), KCl (2), MgCl$_2$ (1), CaCl$_2$ (1.8), HEPES (hemi-Na salt; 5) supplemented with sodium pyruvate (2.5), theophylline (0.5), and 50 µg/ml$^{-1}$ gentamycin for 2-5 days post-injection.

GABA$_C$ Receptor Electrophysiological Assay

Electrophysiological methods were performed as previously described. Hertz L, Juurlink B H J, Hertz E, Fosmark H and Schousboe A. Preparation of Primary Cultures of Mouse (Rat) Astrocytes, in A Dissection and Tissue Culture Mnual of the Nervous System (Shahar A, de Vellis J, Vernadakis A and Haber B eds) pp 105-108, Alan R. Liss, Inc., New York, 1989 Stage V-VI oocytes were injected with 10 ng 50 nl$^{-1}$ of ρ1 mRNA and then stored at 16° C. Recordings of receptor activity were obtained for 2-5 days by a two-electrode voltage clamp by means of a Geneclamp 500 amplifier (Axon Instruments Inc., Foster City, Calif.), a MacLab 2e recorder (AD Instruments, Sydney, NSW), and Chart version 3.6.3 program. Oocytes were voltage clamped at −60 mV, and the preparation was continually perfused with ND96 solution at room temperature. Compound 2 (CPP-115) (100 µM) dissolved in ND96 was applied in the absence and presence of GABA, respectively, until maximum current was reached, at which time the oocytes were washed for 5 to 10 min to allow complete recovery of response to GABA (1 µM). Compound 2 (CPP-115) was tested on three oocytes from at least two harvests.

Cocaine-Induced Conditioned Place Preference (CPP)

A non-biased approach was used for all CPP studies. Specifically, animals were pretested in the CPP chambers for a pre-existing chamber bias. Any animals that spent more than 70% of their time in any chamber were eliminated from the study. Thus, only animals that demonstrated no pre-existing chamber bias were used in the study.

In all rodent studies (n=8/group) animals were allowed to acclimate to the animal housing facility for at least 5 days prior to beginning the experiments. CPP chambers were used as previously described, (Ashby, C. R., Jr.; Paul, M.; Gardner, E. L.; Gerasimov, M. R.; Dewey, S. L.; Lennon, I. C.; Taylor, S. J. C. Systemic administration of 1R,4S-4-amino-cyclopent-2-ene-carboxylic acid, a reversible inhibitor of GABA transaminase, blocks expression of conditioned place preference to cocaine and nicotine in rats. *Synapse* (New York, N.Y., United States) 2002, 44(2), 61-63.) except instead of one chamber being entirely white and the other black, one chamber was entirely light blue with a stainless steel floor, and the second chamber was light blue with horizontal black stripes (2.5 cm wide) spaced 3.8 cm apart with a smooth Plexiglass floor. In all CPP studies with 2, the saline volume was (1 ml/kg), the cocaine doses were 20 mg/kg, and the dosage of 2 was 1.0 mg/kg. The saline, cocaine, and Compound 2 (CPP-115) were all injected intraperitoneally (i.p.). The conditioning procedure for the acquisition phase consisted of 12 sessions carried out consecutively over 12 days. The CPP pairings were: 1) saline/saline; 2) saline/cocaine; 3) Compound 2 (CPP-115)/saline, and 4) saline/cocaine+Compound 2 (CPP-115). Animals in each group were randomly assigned to a 2×2 factorial design with one factor being the pairing chamber and the other factor being the order of conditioning.

Animals that received either saline or cocaine were injected and confined to the appropriate compartment for 30 min. (1S,3S)-3-amino-4-difluoromethylenyl-1-cyclopentanoic acid injections were given 2.5 h prior to saline or cocaine injections. This was done as it has been shown that GABA levels reach maximal values 3 to 4 h following the administration of (1S,3S)-3-amino-4-difluoromethylenyl-1-cyclopentanoic acid. On the test day (day 12) neither drugs nor saline was administered, and the animals were allowed to move freely between both chambers for 15 min. The amount of time spent in each chamber was recorded using an automated infrared beam electronically coupled to a timer. For the expression phase of CPP to cocaine, the animals were habituated and conditioned to cocaine as described in the acquisition studies, but no animals in the expression studies were given 2 on conditioning days. On the test day, the animals being tested received either saline or Compound 2 (CPP-115) 2.5 h prior to their being placed in the apparatus and allowed free access to both chambers for 15 min. A time period of 2.5 hours was selected because previous studies demonstrated that this was the optimal pretreatment interval allowing for a maximal increase in GABA concentrations. Dewey, S. L.; Morgan, A. E.; Ashby Jr., C. R.; Horan, B.; Kushner, S. A.; Logan, J.; Volkow, N. D.; Fowler, J. S.; Gardner, E. L.; Brodie, J. D. A novel strategy for the treatment of cocaine addiction. *Synapse* 1998, 30, 119-129.

µPET Imaging Studies

Using separate adult animals (male Sprague-Dawley rats, n=2) µPET studies were performed using a Concorde Microsystems R4. Baseline $^{11}$C-raclopride binding was examined in anesthetized (ketamine/xylazine) animals. $^{11}$C-raclopride (20.4 min half-life) is selective for the dopamine family of receptors and competes directly with dopamine for receptor binding. Thus, drug-induced increases in brain dopamine produce a decrease in $^{11}$C-raclopride binding while dopamine depletion produces an increase in binding. Approximately 2 h following these baseline scans, animals received an intravenous injection of cocaine (5 mg/kg) followed 5 min later by a second injection of $^{11}$C-raclopride. Approximately 2 h following this scanning session, animals received compound (1S,3S)-3-amino-4-difluoromethylenyl-1-cyclopentanoic acid (0.5 mg/kg). Approximately 2.5 h following the administration of (1S,3S)-3-amino-4-difluoromethylenyl-1-cyclopentanoic acid, animals received a second intravenous dose of cocaine (5.0 mg/kg) followed 5 min later with a third injection of $^{11}$C-raclopride.

Effects of (1S,3S)-3-amino-4-difluoromethylenyl-1-cyclopentanoic acid (2) at GABA Transporters and Receptors Interaction of (1S,3S)-3-amino-4-difluoromethylenyl-1-cyclopentanoic acid with GABA transporters.

(1S,3S)-3-amino-4-difluoromethylenyl-1-cyclopentanoic acid displayed no inhibitory activity at 1 mM concentration at GABA transporters in neurons, astrocytes, or mammalian cells recombinantly expressing human or mouse transporter subtypes (Table 1). The pharmacological properties of (1S,3S)-3-amino-4-difluoromethylenyl-1-cyclopentanoic acid were characterized in tsA201 or HEK293 cells transiently expressing the four human or mouse GABA transporter subtypes (human hGAT-1, hBGT-1, hGAT-2, hGAT-3, and mouse mGAT1-4, respectively).

TABLE 1

Effects of GABA and Compound 2 (CPP-115) on GABA uptake in neurons, astrocytes, and human and mouse GABA transporter-expressing cells

| | (1S,3S)-3-amino-4-difluoromethylenyl-1-cyclopentanoic acid IC$_{50}$ (µM) | GABA IC$_{50}$ (µM) |
|---|---|---|
| hGAT-1 uptake | >1000 | 10[a] |
| hBGT-1 uptake | >1000 | 26[a] |
| hGAT-2 uptake | >1000 | 11[a] |
| hGAT-3 uptake | >1000 | 10[a] |
| mGAT1 uptake | >1000 | 17[b] |
| mGAT2 uptake | >1000 | 51[b] |
| mGAT3 uptake | >1000 | 15[b] |

TABLE 1-continued

Effects of GABA and Compound 2 (CPP-115) on GABA uptake in neurons, astrocytes, and human and mouse GABA transporter-expressing cells

| | (1S,3S)-3-amino-4-difluoromethylenyl-1-cyclopentanoic acid IC$_{50}$ (µM) | GABA IC$_{50}$ (µM) |
|---|---|---|
| mGAT4 uptake | >1000 | 17[b] |
| neuron uptake | >1000 | 8[b] |
| astrocyte uptake | >1000 | 32[b] |

[a]data from Kvist, T.; Christiansen, B.; Jensen, A. A.; Bräuner-Osborne, H. The four human gamma aminobutyric acid (GABA) transporters: pharmacological characterization and validation of a highly efficient screening assay.*Comb. Chem. High Throughput Screen* 2009, 12, 241-249
[b]data from Bolvig T, Larsson O M, Pickering D S, Nelson N, Falch E, Krogsgaard-Larsen P and Schousboe A. Action of Bicyclic Isoxazole GABA Analogues on GABA Transporters and Its Relation to Anticonvulsant Activity. *Eur. J. Pharmacol.* 1999, 375, 367-374.

Figure 1:
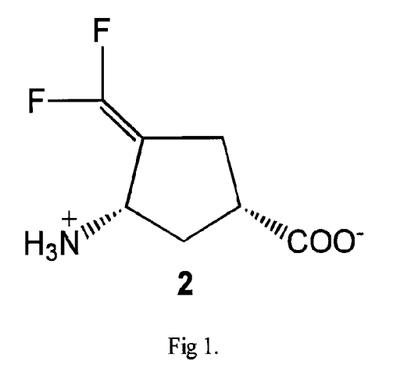
FIG. 1 is the structure for (1S,3S)-3-amino-4-difluoromethylenyl-1-cyclopentanoic acid

Interaction of (1S,3S)-3-amino-4-difluoromethylenyl-1-cyclopentanoic acid with GABA Receptors To investigate a possible interaction of (1S,3S)-3-amino-4-difluoromethylenyl-1-cyclopentanoic acid with GABA receptors, the compound was tested for its ability to displace [3H]GABA binding to ionotropic GABA$_A$ receptors or metabotropic GABA$_B$ receptors in rat brain cortical homogenate. At a concentration of 100 µM, no inhibition of binding was observed at either receptor tested, whereas 1 mM cold GABA inhibited radioligand binding as expected (Table 2). Furthermore, (1S,3S)-3-amino-4-difluoromethylenyl-1-cyclopentanoic acid was tested for activity at recombinant human ρ1 GABA$_C$ receptors expressed in oocytes and was found to exhibit no effect as an agonist or antagonist at a concentration of 100 µM (FIG. 1).

TABLE 2

Effect of (1S,3S)-3-amino-4-difluoromethylenyl-1-cyclopentanoic acid on GABA$_A$ and GABA$_B$ receptors evaluated in binding assays

| | IC$_{50}$ (µM) | |
|---|---|---|
| | (1S,3S)-3-amino-4-difluoromethylenyl-1-cyclopentanoic acid | GABA |
| [3H]muscimol competition (GABA$_A$ receptor) | >100 | 0.049[a] |
| [3H]GABA competition[b] (GABA$_B$ receptor) | >100 | 0.013[a] |

[a]data from Wellendorph, P.; Høg, S.; Greenwood, J. R.; de Lichtenberg, A.; Nielsen, B.; Frølund, B.; Brehm, L.; Clausen, R. P.; Bräuner-Osborne, H. Novel cyclic gamma-hydroxybutyrate (GHB) analogs with high affinity and stereoselectivity of binding to GHB sites in rat brain. *J. Pharmacol. Exp. Ther.* 2005, 375, 346-351.
[b]a high concentration of isoguvacine was added to ensure saturation of GABA$_A$ receptor sites Cocaine-Induced Conditioned Place Preference (CPP) Studies Effect of compound (1S,3S)-3-amino-4-difluoromethylenyl-1-cyclopentanoic acid on dopamine release from nucleus accumbens (NAc) by cocaine administration to rats.

To compare the pharmacological effects of (1S,3S)-3-amino-4-difluoromethylenyl-1-cyclopentanoic acid to the previously reported effect of vigabatrin, the effect of cocaine administration on NAc-released dopamine was determined In these preliminary µPET imaging studies, cocaine reduced $^{11}$C-raclopride binding by an average of 22%, consistent with an increase in synaptic dopamine. However, when treated with (1S,3S)-3-amino-4-difluoromethylenyl-1-cyclopentanoic acid, there was no effect of cocaine on $^{11}$C-raclopride binding. That is, $^{11}$C-raclopride binding was similar to the control data, consistent with (1S,3S)-3-amino-4-difluoromethylenyl-1-cyclopentanoic acid (0.5 mg/kg) producing a complete blockade of cocaine-induced increases in synaptic dopamine at a dose 600 times lower than the 300 mg/kg dose of vigabatrin that was effective previously. Ashby, C. R., Jr.; Rohatgi, R. i; Ngosuwan, J.; Borda, T.; Gerasimov, M. R.; Morgan, A. E.; Kushner, S.; Brodie, J. D.; Dewey, S. L. Implication of the $GABA_B$ receptor in gamma vinyl-GABA's inhibition of cocaine-induced increases in nucleus accumbens dopamine. *Synapse* (New York) 1999, 31(2), 151-153.

Effect of (1S,3S)-3-amino-4-difluoromethylenyl-1-cyclopentanoic Acid on the Expression of CPP Increases in NAc dopamine following administration of cocaine produces a dose-dependent and profound effect on the expression of CPP in rats. CPP is a well-documented model that assesses the saliency of drugs of abuse in a drug-free state. The ability to pharmacologically block the expression of a cocaine-induced CPP suggests that these compounds might have an indication for treating cocaine addiction.

Cocaine produced a dose-dependent CPP response, with the most reliable and robust response occurring at 20 mg/kg. Therefore, we chose a 20 mg/kg cocaine dose with which to examine the effect of the administration of (1S,3S)-3-amino-4-difluoromethylenyl-1-cyclopentanoic acid on the expression of a cocaine-induced CPP. The results clearly indicate that 1.0 mg/kg of 2 blocked the expression of cocaine-induced CPP. By itself, (1S,3S)-3-amino-4-difluoromethylenyl-1-cyclopentanoic acid produced neither a CPP nor a conditioned aversive response, indicating that 2 exhibits no abuse potential. These data are interesting in that similar findings with vigabatrin required a dose of 300 mg/kg, while the effects of (1S,3S)-3-amino-4-difluoromethylenyl-1-cyclopentanoic acid were obtained using a dose of only 1.0 mg/kg. Specifically, in the saline/saline pairings, animals spent an equal amount of time in both chambers (7.2±2.2 versus 7.8±2.9 min). However, in the saline/cocaine pairings, animals spent a significantly greater amount of time in the cocaine-paired chamber 12.2±1.7 versus 4.8±2.8 min ($p<0.01$, Student's two-tailed t-test). In the saline/Compound 2 (CPP-115) pairings, animals spent an equal amount of time in both chambers (8.1±3.2 versus 6.9±3.9 min), suggesting that (1S,3S)-3-amino-4-difluoromethylenyl-1-cyclopentanoic acid did not produce a CPP on its own. In the cocaine/saline+(1S,3S)-3-amino-4-difluoromethylenyl-1-cyclopentanoic acid pairings, animals again spent an equal amount of time in both chambers (7.9±1.5 versus 7.1±1.9 min), demonstrating that at a dose of 1.0 mg/kg, (1S,3S)-3-amino-4-difluoromethylenyl-1-cyclopentanoic acid completely blocked the expression of a cocaine-induced CPP, which is 300 times the effect of vigabatrin.

Because of the importance of GABAergic effects on a variety of neurological disorders and the inherent complexity of this system resulting from multiple subtypes of receptors and transporters, it is crucial that potential therapeutic compounds are selective for specific components of the GABAergic system. In this study we evaluated the selectivity profile of a recently described GABA-AT inhibitor, (1S,3S)-3-amino-4-difluoromethylenyl-1-cyclopentanoic acid (2). We find that (1S,3S)-3-amino-4-difluoromethylenyl-1-cyclopentanoic acid does not affect GABA uptake in recombinantly expressed human and mouse GABA transporters or in mouse cortical astrocytes or neurons. Furthermore, (1S,3S)-3-amino-4-difluoromethylenyl-1-cyclopentanoic acid displays no affinity for $GABA_A$ or $GABA_B$ receptors and is neither an agonist nor an antagonist for $GABA_C$ receptors. Although (1S,3S)-3-amino-4-difluoromethylenyl-1-cyclopentanoic acid was not tested for functional activity at $GABA_A$ and $GABA_B$ receptors, thus not ruling out a possible allosteric mechanism, the structural resemblance of (1S,3S)-3-amino-4-difluoromethylenyl-1-cyclopentanoic acid to GABA justifies ruling out binding to the GABA site over allosteric site. As previously reported, the principal GABAergic site of action of (1S,3S)-3-amino-4-difluoromethylenyl-1-cyclopentanoic acid appears to be GABA-AT, the enzyme that catabolizes GABA. Sherif, F. M.; Ahmed, S. S. Basic aspects of GABA transaminase in neuropsychiatric disorders. *Clin. Biochem.* 1995, 28(2), 145-54. Because of the effectiveness of vigabatrin, an irreversible inactivator of GABA-AT, on the reversal of specific addiction-associated biochemical and behavioral measures to a variety of drugs of abuse, (1S,3S)-3-amino-4-difluoromethylenyl-1-cyclopentanoic acid was investigated for its ability to block cocaine-induced increases in NAc dopamine concentrations by μPET in sedated animals, an indicator of addictive behavior. Further, we extended these biochemical findings to a behavioral measure, the expression of a cocaine-induced CPP.

It is likely that the smaller increase in NAc dopamine levels produced by an acute cocaine challenge following either pretreatment with vigabatrin or (1S,3S)-3-amino-4-difluoromethylenyl-1-cyclopentanoic acid is what underlies the effects we observed in both the μPET imaging and the CPP studies. In fact, we observed that a dose of (1S,3S)-3-amino-4-difluoromethylenyl-1-cyclopentanoic acid that is 1/300 (1.0 mg/kg) to 1/600 (0.5 mg/kg) that of vigabatrin (300 mg/kg) completely reversed cocaine-induced increases in synaptic dopamine as well as in the expression of a cocaine-induced CPP. Given the effectiveness and visual safety of vigabatrin in clinical trials for the treatment of cocaine and/or methamphetamine addiction, in combination with its pre-clinical efficacy for the treatment of nicotine, methamphetamine, heroin, and ethanol abuse, it is likely that (1S,3S)-3-amino-4-difluoromethylenyl-1-cyclopentanoic acid also will be effective in treating these addictive behaviors in humans. The potential advantage of (1S,3S)-3-amino-4-difluoromethylenyl-1-cyclopentanoic acid, however, is its much greater potency relative to vigabatrin, which could markedly reduce its daily dosage relative to that of vigabatrin (1-3 g/day). Furthermore, given the visual adverse effects of vigabatrin frequently reported after long-term use in relation to its epilepsy indication, (1S,3S)-3-amino-4-difluoromethylenyl-1-cyclopentanoic acid has been evaluated for visual side effects to possibly provide an alternative to vigabatrin for epilepsy patients internationally. If the predominant cause of visual field defect in vigabatrin therapy is not due to elevated GABA, as has been argued by some researchers, (Sills, G. J.; Butler, E.; Forrest, G.; Ratnaraj, N.; Patsalos, P. N.; Brodie, M. J. Vigabatrin, but not gabapentin or topiramate, produces concentration-related effects on enzymes and intermediates of the GABA shunt in rat brain and retina. *Epilepsia* 2003, 44(7), 886-892) the mechanistic differences between vigabatrin and (1S,3S)-3-amino-4-difluoromethylenyl-1-cyclopentanoic acid with regard to their inactivation of GABA-AT could contribute to less visual field defect in the case of (1S,3S)-3-amino-4-difluoromethylenyl-1-cyclopentanoic acid.

Figure 2:
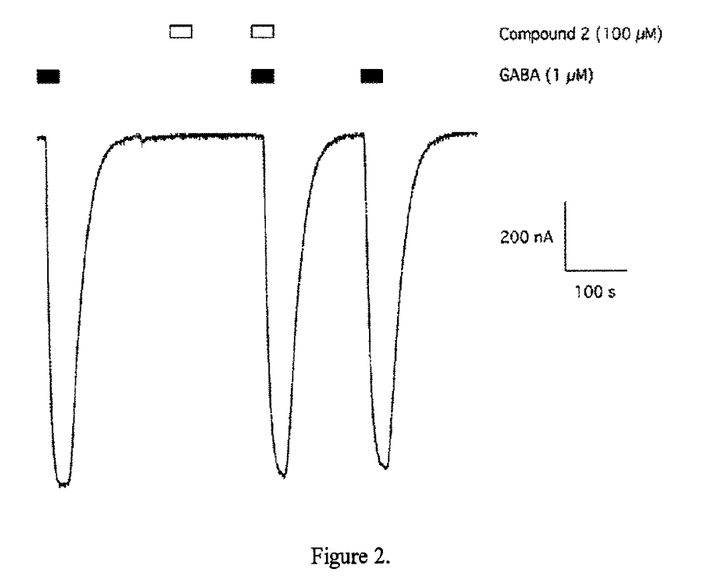
FIG. 2 is a graph showing the effects of (1S,3S)-3-amino-4-difluoromethylenyl-1-cyclopentanoic acid alone and co administered with GABA on oocytes expressing human ρ1 $GABA_C$ receptors.

FIG. 2 shows the effects of GABA and CPP 115 on $GABA_C$. GABA (1 μM; $EC_{80}$) (duration indicated by black bar) activated an inward current in oocytes expressing human ρ1 $GABA_C$ receptors clamped at −60 mV. CPP-115 ((1S,3S)-3-amino-4-difluoromethylenyl-1-cyclopentanoic acid) (100 μM, duration indicated by the white bar) did not activate a current. When co-applied with GABA (1 μM), CPP 115 (100 μM) did not significantly reduce the GABA response ($p>0.05$; n=3; Student t-test).

Figure 3:
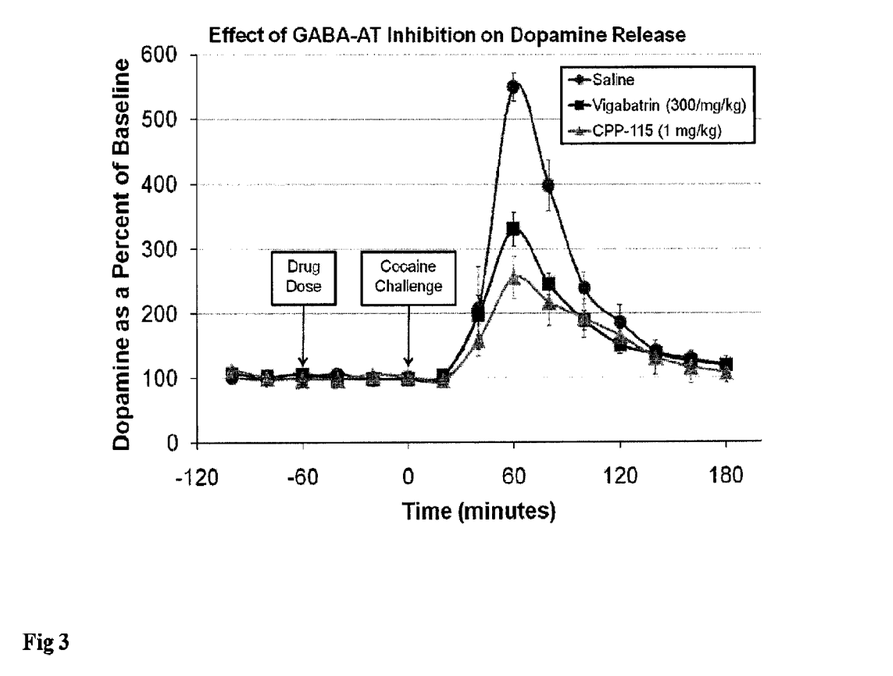
FIG. 3 is a graph comparing the time-dependent effects of (1S,3S)-3-amino-4-difluoromethylenyl-1-cyclopentanoic acid on dopamine release from nucleus accumbens (NAc) by cocaine administration to rats versus vigabatrin and a saline control

FIG. 3 shows the effect of the administration of a single dose of (1S,3S)-3-amino-4-difluoromethylenyl-1-cyclopentanoic acid, vigabatrin or a saline control on a cocaine induced dopamine surge prior to the cocaine challenge. Each drug was administered near their maximally effective therapeutic dose (1 mg/kg and 300 mg/kg), respectively. The levels of dopamine were measured by observing the displacement of $^{11}$C-raclopride from dopamine receptors by the presence of intersynaptic dopamine using positron emission tomography in Sprague Dawley rats. (1S,3S)-3-amino-4-difluoromethylenyl-1-cyclopentanoic acid resulted in a surprising and significantly lower dopamine surge than is achievable with vigabatrin under the same experimental conditions. Dopamine release in the saline control group demonstrated a dopamine increase more than 500 percent of basline. Those animals treated with vigabatrin showed a dopamine increase more that 300 percent of baseline whereas the (1S,3S)-3-amino-4-difluoromethylenyl-1-cyclopentanoic acid group displayed levels less than 300 times baseline. These data show that (1S,3S)-3-amino-4-difluoromethylenyl-1-cyclopentanoic acid is superior to vigabatrin in its ability to reduce a cocaine induced dopamine surge at the maximally effective therapeutic dose of each drug. Such a reduction in the dopamine surge is expected to be more effective in treating cocaine addiction than vigabatrin at doses where GABA-AT is maximally inactivated.

Treatment of Pain and Nervous System Disorders.

Gabaergic drugs are those which improve secretion or transmission of GABA. These drugs as a family have been used to treat a wide variety of nervous system disorders including epilepsy, fibromyalgia, neuropathy, migraines related to epilepsy, restless leg syndrome, and post traumatic distress disorder. Gabaergic drugs include $GABA_A$ and $GABA_B$ receptor ligands, GABA reuptake inhibitors, GABA aminotransferase inhibitors, GABA analogs, or molecules containing GABA itself. Preferred GABAergic drugs include valproate and its derivatives, vigabatrin, pregabalin, gabapentin and tiagabine.

It is proposed that (1S,3S)-3-amino-4-difluoromethylenyl-1-cyclopentanoic acid may be used to treat epilepsy, infantile spasms fibromyalgia, neuropathy, migraines related to epilepsy, restless leg syndrome, and post traumatic distress disorder at significantly lower doses that currently approved Gabaergic drugs.

Published United States patent application number 20040023952 A1, Ser. No. 10/311,821, entitled *Enhanced Brain Function by GABA-ergic Stimulation* describes how gabaergic drugs are useful in treating variety of age-associated disorders of cortical decline in the elderly. These "age-associated" disorders of cortical decline extend on a continuum from normal age-related senescence to severe dementias associated with Alzheimer's disease and Parkinson's disease in an aging population. Published patent application 20040023952 A1 is expressly incorporated herein by reference.

U.S. Pat. No. 6,939,876 describes and/or claims the use of vigabatrin in the treatment to prevent addiction to opioid analgesics by co administration of vigabatrin. The contents of U.S. Pat. No. 6,939,876 is expressly incorporated herein by reference. It is believed that (1S,3S)-3-amino-4-difluoromethylenyl-1-cyclopentanoic acid will prevent addiction to opioid analgesics by administering the (1S,3S)-3-amino-4-difluoromethylenyl-1-cyclopentanoic acid to the patient before, with or after administration of the opioid.

GABA aminotransferase inhibitors have been shown to be effective for treatment of obsessive compulsive disorders including general anxiety disorder, pathological or compulsive gambling disorder, compulsive eating (obesity), body dysmorphic disorder, hypochondriasis, pathologic grooming conditions, kleptomania, pyromania, attention deficit hyperactivity disorder and impulse control disorders in U.S. Pat. No. 6,462,084, which is expressly incorporated by reference. Because (1S,3S)-3-amino-4-difluoromethylenyl-1-cyclopentanoic acid is a GABA aminotransferase inhibitor, it is anticipated it will have the same activity but without the visual field defects and at doses between 1/100 to about 1/700 the dose of vigabatrin.

Dosages of (1S,3S)-3-amino-4-difluoromethylenyl-1-cyclopentanoic acid are anticipated to be 2 to 2.5 mg/kg/day for treatment of epilepsy or about 140-175 mg/day for an average 70 kg adult. The dose for treatment of addiction is expected to be only 0.05 to 0.2 mg/kg/day, or about 3.0-15 mg/day for the average 70 kg adult.

The mechanism of inactivation of GABA is known. Nanavati, Shrenik M., Silverman, Richard B. Mechanisms of inactivation of gamma-aminobutyric acid aminotransferase by the antiepilepsy drug gaba vinyl GABA (vigabatrin). *J. Am. Chem. Society*, 1991 113(24), 9341-9349; Pan, Yue, et al. Design, Synthesis and Biological Activity of a DiFluoro-Substituted Conformationally Rigid Vigabatrin Analogue as a Potent Aminobutyric Acid Aminotransferase Inhibitor. *J. Med. Chem.* 2003, 46(25) 5292-5293).

Figure 4:
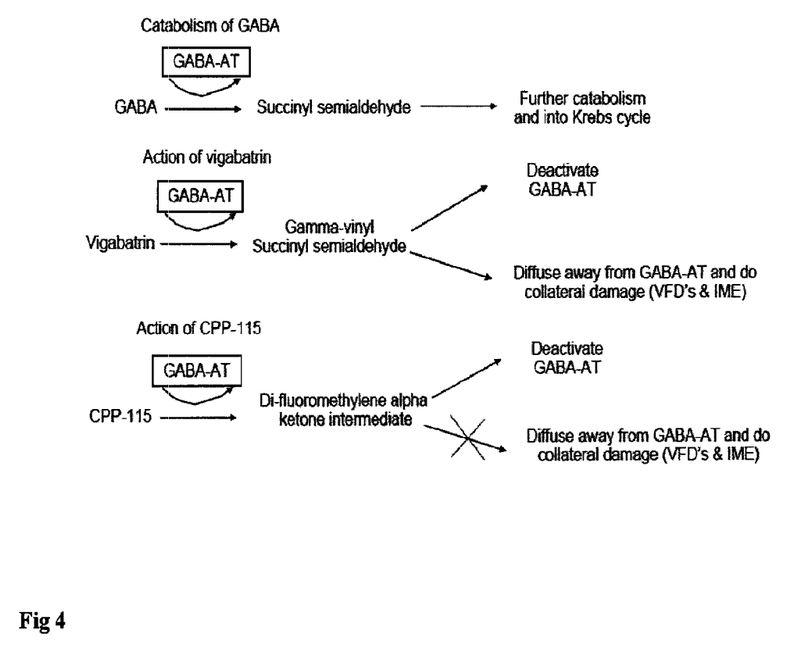
FIG. 4 is a diagram illustrating a hypothetical explanation of why (1S,3S)-3-amino-4-difluoromethylenyl-1-cyclopentanoic acid is likely to reduce collateral damage to the retina and neurological structures.

Without wishing to be limited in theory, applicants believe that (1S,3S)-3-amino-4-difluoromethylenyl-1-cyclopentanoic acid will not cause or will significantly reduce visual defect damage as compared to vigabatrin at equally efficacious doses of both drugs. Referring to FIG. 4, which shows a diagram of why (1S,3S)-3-amino-4-difluoromethylenyl-1-cyclopentanoic acid (CPP-115) is not expected to cause collateral damage including visual field defects. Some vigabatrin molecules directly inactivate the GABA aminotransferase molecule upon binding. A small amount of the vigabatrin however, upon binding to GABA aminotransferase, is converted to 4-oxohex-5-enoic acid, which might diffuse away from the binding site. Due to the reactivity of 4-oxohex-5-enoic acid, it could readily bind to other molecules with functional groups containing free electron pairs (e.g., $NH_2$.). This could cause the collateral damage including, but not limited to, visual field defects and intramyelinic edema.

The mechanism leading to the collateral damage is not known. The damage might occur from the toxic effects of elevated GABA resulting from the inactivation of GABA-AT, could be a direct toxic effect, could be the consequence of an enzymatically produced byproduct from the inactivation of GABA-AT, or some combination thereof. The applicants have hypothesized that an alpha-beta unsaturated ketone byproduct resulting from the action of GABA-AT on the inactivator molecule. (1S,3S)-3-amino-4-difluoromethylenyl-1-cyclopentanoic acid was specifically designed to either inactivate the enzyme by an alternate mechanism or to form an intermediate that is much more reactive. This more reactive intermediate, if formed, would immediately inactivate the enzyme before it could diffuse into the cytoplasm, thus limiting the potential for collateral damage to other cellular structures.

Because of the low rate at which vigabatrin actually inactivates the GABA aminotransferase enzyme, vigabatrin is given in higher doses which results in 4-oxohex-5-enoic acid being present in higher quantities with greater opportunity to cause collateral damage.

In contrast, it is believed that the (1S,3S)-3-amino-4-difluoromethylenyl-1-cyclopentanoic acid upon oxidation by the GABA aminotransferase immediately inactivates the enzyme because of the highly reactive di-fluoromethylene intermediate, which results from administration of (1S,3S)-3-amino-4-difluoromethylenyl-1-cyclopentanoic acid. It is hypothesized that (1S,3S)-3-amino-4-difluoromethylenyl-1-cyclopentanoic acid is more thermodynamically favorable for both staying bound to the binding site and for inducing the conformational changes in GABA aminotransferase upon inactivation of the enzyme. Collateral damage is believe to be avoided because the (1S,3S)-3-amino-4-difluoromethylenyl-1-cyclopentanoic acid upon amine oxidation immediately inactivates the GABA aminotransferase and remains bound to the enzyme. Because the reactive intermediate remains bound to the molecule, it is not free to react with other molecules and therefore does not produce the collateral damage. Further, because (1S,3S)-3-amino-4-difluoromethylenyl-1-cyclopentanoic acid will be dosed at levels that are more than 100 times lower than vigabatrin, the potential number of reactive intermediate species is significantly reduced.

Visual Field Experiments

Experiments were conducted to test the hypothesis that (1S,3S)-3-amino-4-difluoromethylenyl-1-cyclopentanoic acid reduces visual field defects.

Materials and Methods

Forty-five male and female Wistar Albino rats (Charles River Laboratories), 9 weeks of age at the start of dosing, were acclimated, and placed into one of three treatment groups (vehicle, (1S,3S)-3-amino-4-difluoromethylenyl-1-cyclopentanoic acid (CPP-115) or Vigabatrin). Animals received a single intra-peritoneal injection of vehicle or test formulations once daily for either 45 or 90 consecutive days at 0, 20 or 200 mg/kg for the vehicle, (1S,3S)-3-amino-4-difluoromethylenyl-1-cyclopentanoic acid (CPP-115) and Vigabatrin treatment groups, respectively. The formulations for each treatment group were prepared fresh weekly in 0.9% normal saline.

All animals were acclimated for 7 days to the test facility prior to the start of dosing and were housed in individual polycarbonate cages. The cage environment uses a standard 12 hr/12 hr light dark cycle, with standard industrial fluorescent lighting during the light cycle. During the course of the study, the animals were monitored for mortality, moribundity, clinical signs of illness, feed intake, and body weight change. Any animals found in distress for more than 24 hours were humanely euthanized. Due to the sedative effects of both (1S,3S)-3-amino-4-difluoromethylenyl-1-cyclopentanoic acid (CPP-115) and Vigabatrin, some animals received special food supplements and/or IP fluids in the first 3 weeks of dosing. By the end of the third week of the dosing, the sedative effects of both drugs decreased, and no special food supplements or IP fluids were required. At the conclusion of the dosing phase (5 of each sex for 45 days and 10 of each sex for 90 days), the animals entered a 5-7 day "washout" period, after which electroretinograms (ERGs) were measured for both eyes. The animals were then humanely euthanized, by $CO_2$ asphyxiation in accordance with AVMA guidelines on euthanasia, for post-mortem pathology examinations.

Electroretinogram Recordings

Following a dark adaptation period of at least 12 hours, each eye was dilated with tropicamide (1 drop of 1% solution) and phenylepherine (1 drop of 10% solution), an anesthetic dose of Ketamine HCl (up to 55 mg/kg) and Xylazine HCl (up to 12 mg/kg) was administered IM or IP, and just prior to the ERG, a topical anesthesia (0.5% Proparacaine HCl) was applied to the eye. The types of electroretinogram measurements made and the electroretinogram testing parameters are found in Table 4.

TABLE 4

| ERG type | Flashes/interval | Flash Mode | Pulse Period | Intensity |
| --- | --- | --- | --- | --- |
| Rod | 5 @ 500 ms | Pulse | 4 ms | 0.02 cd · s/m$^2$ |
| Standard Combined | 5 @ 40000 ms | Pulse | 4 ms | 7 cd · s/m$^2$ |
| Light Adaptation | 0 @ 900 sec | N/A | N/A | 25 cd/m$^2$ |
| Single Flash - Cone | 5 @ 15000 ms | Pulse | 4 ms | 6 cd · s/m$^2$ |
| 10 Hz Flicker | 20 | Continuous | 4 ms | 3 cd · s/m$^2$ |
| 15 Hz Flicker | 20 | Continuous | 4 ms | 3 cd · s/m$^2$ |

The electroretinograms were measured with an Espion$^2$ ERG system with ColorDome Ganzfeld type illuminator by Diagnosys. All light stimuli were white light. The ground electrode was a Grass needle electrode inserted sub-cutaneously at the base of the tail. The reference electrode was a Grass gold disc electrode placed on the tongue. The eye electrode was a gold wire. Data was collected on a dual channel system (1 channel per eye) at 1000 samples per second with a $2^{nd}$ order 0.3 Hz to 300 Hz band pass Bessel filter and also a 60 Hz notch filter to remove interference from the line power.

Results

Figure 5:
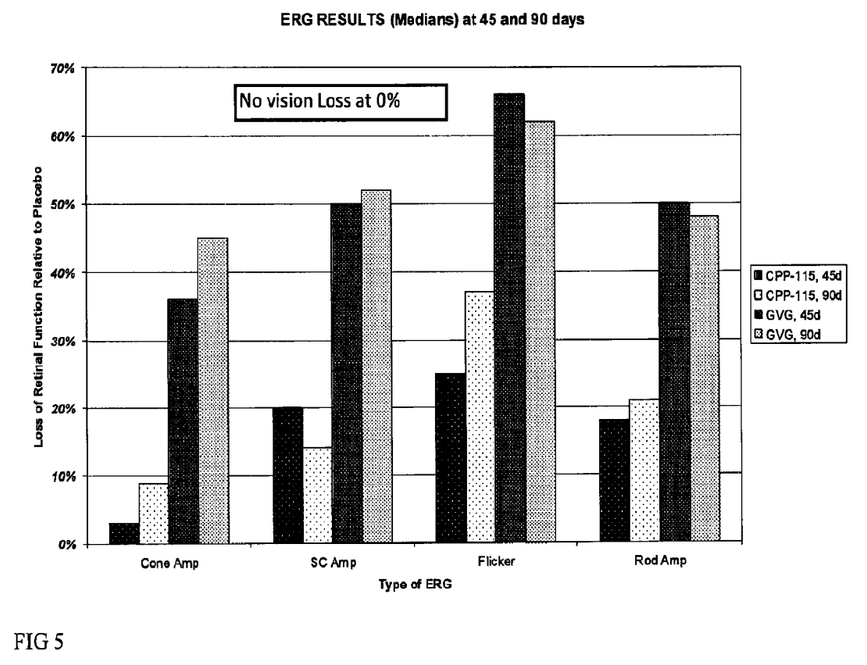
FIG. 5 is a chart summarizing the results of visual field testing data at 45 and 90 days

The results are shown for the right eye in Table 5 below and for the left eye in Table 6. The combined data are summarized in FIG. 5. At the maximum tolerated doses, (1S,3S)-3-amino-4-difluoromethylenyl-1-cyclopentanoic acid caused much less damage and had a much larger margin between the therapeutic dose for addiction and the maximum tolerated dose when compared to vigabatrin. These data clearly show that (1S,3S)-3-amino-4-difluoromethylenyl-1-cyclopentanoic acidcauses less visual field defects than vigabatrin. For the treatment of chronic disorders, risk of visual field defects may be reduced or eliminated by administration of (1S,3S)-3-amino-4-difluoromethylenyl-1-cyclopentanoic acid. This data is even more compelling given the fact that the predicted therapeutic dose of CPP-115 is one twentieth of the dosage given in this experiment. The predicted therapeutic dose of CPP-115 is 1 mg/kg. Vigabatrin however was dosed at its therapeutic dosage.

TABLE 5

Right Eye Data

OD

| Group | A-wave amplitude | | | A-wave Implicit Time | | | B-wave amplitude | | |
|---|---|---|---|---|---|---|---|---|---|
| | Rods | Std Combined | Std Cone | Rods | Std Combined | Std Cone | Rods | Std Combined | Std Cone |
| Control | 26.954 | 121.16 | 6.2527 | 25.7 | 10.2 | 11.6 | 296.99 | 428.6 | 64.026 |
| CPP-115 | 32.53 | 99.93125 | 2.203125 | 27.875 | 9.75 | 10 | 233.8125 | 313.5375 | 59.97875 |
| Vigab | 32.3765 | 81.30125 | 4.744 | 27.75 | 18.375 | 12.125 | 180.35125 | 276.425 | 59.69125 |

OD

| Group | B-wave Implicit Time | | | OP | Average | |
|---|---|---|---|---|---|---|
| | Rods | Std Combined | Std Cone | Std Combined | 10 hz Flicker | 15 hz Flicker |
| Control | 70.6 | 66.4 | 42.4 | 17.4118 | 54.978 | 38.54 |
| CPP-115 | 72.25 | 66 | 42.75 | 11.77125 | 47.43 | 33.11575 |
| Vigab | 92.75 | 74.5 | 52.125 | 7.053 | 27.74975 | 21.201 |

Diff from Control

OD

| Group | A-wave amplitude | | | A-wave Implicit Time | | | B-wave amplitude | | |
|---|---|---|---|---|---|---|---|---|---|
| | Rods | Std Combined | Std Cone | Rods | Std Combined | Std Cone | Rods | Std Combined | Std Cone |
| CPP-115 | 5.576 | −21.22875 | −4.049575 | 2.175 | −0.45 | −1.6 | −63.1775 | −115.0625 | −4.04725 |
| Vigab | 5.4225 | −39.85875 | −1.5087 | 2.05 | 8.175 | 0.525 | −116.63875 | −152.175 | −4.33475 |

OD

| Group | B-wave Implicit Time | | | OP | Average | |
|---|---|---|---|---|---|---|
| | Rods | Std Combined | Std Cone | Std Combined | 10 hz Flicker | 15 hz Flicker |
| CPP-115 | 1.65 | −0.4 | 0.35 | −5.64055 | −7.548 | −5.42425 |
| Vigab | 22.15 | 8.1 | 9.725 | −10.3588 | −27.22825 | −17.339 |

TABLE 6

Left Eye Data

OS

| Group | A-wave amplitude | | | A-wave Implicit Time | | | B-wave amplitude | | | Rods |
|---|---|---|---|---|---|---|---|---|---|---|
| | Rods | Std Combined | Std Cone | Rods | Std Combined | Std Cone | Rods | Std Combined | Std Cone | |
| Control | 27.1097 | 102.762 | 7.0849 | 26.1 | 10.6 | 12.1 | 267.88 | 361.52 | 72.3 | 70.2 |
| CPP-115 | 37.06625 | 107.88125 | 4.380625 | 28.5 | 9.75 | 14.25 | 261.4375 | 335.9 | 55.5825 | 71.5 |
| Vigab | 24.284625 | 66.0375 | 3.737625 | 28.75 | 18.75 | 12.375 | 151.20125 | 219.4775 | 40.1925 | 89 |

OS

| Group | B-wave Implicit Time | | OP | Average | |
|---|---|---|---|---|---|
| | Std Combined | Std Cone | Std Combined | 10 hz Flicker | 15 hz Flicker |
| Control | 67.4 | 45 | 14.984 | 56.662 | 39.538 |
| CPP-115 | 77.625 | 43.5 | 12.172125 | 42.79875 | 29.187 |
| Vigab | 77.5 | 47.625 | 6.367625 | 19.072125 | 14.8 |

Diff from Control

TABLE 6-continued

Left Eye Data

OS

| Group | A-wave amplitude | | | | A-wave Implicit Time | | | B-wave amplitude | | |
|---|---|---|---|---|---|---|---|---|---|---|
| | Rods | Std Combined | Std Cone | Rods | Std Combined | Std Cone | Rods | Std Combined | Std Cone | Rods |
| CPP-115 | 9.95655 | 5.11925 | −2.70428 | 2.4 | −0.85 | 2.15 | −6.4425 | −25.62 | −16.7175 | 1.3 |
| Vigab | −2.825075 | −36.7245 | −3.34728 | 2.65 | 8.15 | 0.275 | −116.67875 | −142.0425 | −32.1075 | 18.8 |

OS

| Group | B-wave Implicit Time | | OP | Average | |
|---|---|---|---|---|---|
| | Std Combined | Std Cone | Std Combined | 10 hz Flicker | 15 hz Flicker |
| CPP-115 | 10.225 | −1.5 | −2.811875 | −13.86325 | −10.351 |
| Vigab | 10.1 | 2.625 | −8.616375 | −37.589875 | −24.738 |

Epilepsy Studies

Animal studies were run in epilepsy models comparing vigabatrin and CPP-115 as set out below. Data are summarized in Table 7.

Corneal Kindling

Mice are kindled electrically with 3 sec stimulation, 8 mA, 60 Hz, and corneal electrodes to a criterion of 10 consecutive Stage 5 seizures (facial clonus and head nodding progressing to forelimb clonus, and finally rearing and falling accompanied by a generalized clonic seizure as described by Racine). Stage 5 is generally reached after twice daily stimulation for 8 days. With continued stimulation once a day, animals usually progress to a reproducible Stage 5 after 10-14 additional days. At least 72 hours after the mice have been kindled, the test substance is administered either i.p. or p.o. and, at the previously determined TPE, each animal is given the electrical stimulus indicated above. Following stimulation, the animals are observed for the presence or absence of the rearing and falling criteria of a Stage 5 seizure. Treated animals not displaying a Stage 3, 4, or 5 seizure are considered protected. The dose of the test substance is varied between the limits of 0 and 100% efficacy, and the ED50 (mean effective dose) and 95% confidence intervals calculated by probit analysis. Mean values and the S.E.M. are calculated for the length of clonus and seizure duration and p values are determined by the Student's t-test Maximal Electrical Shock (MES) Model The MES is a model for generalized tonic-clonic seizures and provides an indication of a compound's ability to prevent seizure spread when all neuronal circuits in the brain are maximally active. These seizures are highly reproducible and are electrophysiologically consistent with human seizures. For all tests based on MES convulsions, 60 Hz of alternating current (50 mA in mice) is delivered for 2 s by corneal electrodes which have been primed with an electrolyte solution containing an anesthetic agent (0.5% tetracaine HCL). Mice are tested at various intervals following doses of 30, 100 and 300 mg/kg of test compound given by i.p. injection of a volume of 0.01 mL/g. Other doses can be used if indicated by previously known pharmacology. An animal is considered "protected" from MES-induced seizures upon abolition of the hindlimb tonic extensor component of the seizure (Swinyard et al., 1989; White et al., 1995a; White et al., 1995b).

Subcutaneous Metrazol Seizure Threshold Test (scMET)

Subcutaneous injection of the convulsant Metrazol produces clonic seizures in laboratory animals. The scMET test detects the ability of a test compound to raise the seizure threshold of an animal and thus protect it from exhibiting a clonic seizure. Animals are pretreated with various doses of the test compound given by i.p. injection. At the previously determined TPE of the test compound, the dose of Metrazol which will induce convulsions in 97% of animals (CD97; 85 mg/kg mice) is injected into a loose fold of skin in the midline of the neck. The animals are placed in isolation cages to minimize stress (Swinyard et al, 1961) and observed for the next 30 minutes for the presence or absence of a seizure. An episode of clonic spasms, approximately 3-5 seconds, of the fore and/or hindlimbs, jaws, or vibrissae is taken as the endpoint. Animals which do not meet this criterion are considered protected.

Chemoconvulsant Models—(Subcutaneous Bicuculline (scBic) and Subcutaneous Picrotoxin (scPic))

Bicuculline (Bic) and Picrotoxin (Pic) are chemoconvulsants that cause clonic seizures in a manner similar to Metrazol (see scMET test). Anti-seizure (ASDs) or Anti-epileptic drugs (AEDs) are not always equally effective in protecting against seizures induced by these known convulsant compounds. Therefore, as much as possible it is useful to differentiate novel AEDs pharmacologically. In the scBic and scPic tests, adult male CF No 1 albino mice (18-25 g) are dosed with the test compound via i.p. injection in a volume of 0.01 ml/g of body weight. At a previously determined time of peak effect (TPE), the animals are given a subcutaneous injection of either of the noted chemo-convulsants using the convulsive dose (CD97—a dose of 2.7 or 2.5 mg/kg, for Bic and Pic, respectively). The experimental animals are placed in isolation cages to minimize possible crowding stresses (Swinyard et al., 1961) and observed for the next 30 minutes (for Bic) or 45 minutes (for Pic) for the presence or absence of a seizure. An episode of clonic spasms, approximately 3-5 seconds, of the fore and/or hindlimbs, jaws, or vibrissae is used as the experimental endpoint. Animals which do not meet this criterion are considered protected.

Minimal Clonic Seizure (6 Hz) Test

Some clinically useful AEDs are ineffective in the standard MES and scMET tests but still have anticonvulsant activities in vivo. In order to identify potential AEDs with this profile, compounds may be tested in the minimal clonic seizure (6 Hz or 'psychomotor') test (Barton et al., 2001). Like the maximal electroshock (MES) test, the minimal clonic seizure (6 Hz) test is used to assess a compound's efficacy against electrically induced seizures but uses a lower frequency (6 Hz) and longer duration of stimulation (3 s). Test compounds are pre-administered to mice via i.p. injection. At varying times, individual mice (four per time point) are challenged with sufficient current delivered through corneal electrodes to elicit a psychomotor seizure in 97% of animals (32 mA for 3 s) (Toman et al., 1952). Untreated mice will display seizures characterized by a minimal clonic phase followed by stereotyped, automatistic behaviors described originally as being similar to the aura of human patients with partial seizures. Animals not displaying this behavior are considered protected. The test may be evaluated quantitatively by measuring the responses at varying doses at a determined time of peak effect (TPE). This test may also be conducted at 22 and 44 mA if requested by ASP staff.

TABLE 7

Epilepsy Model Effectiveness Data for Vigabatrin (GVG) and CPP-115

| Test | Conditions | Species | CPP-115 ASP# 424003 | GVG ASP# 424019 |
|---|---|---|---|---|
| 6 Hz | Single IP drug dose, 6 Hz, 44 mA, 3 seconds, corneal electrode | Mice | $ED_{50}$ = 28.4 mg/kg TPE 4 hours | $ED_{50}$ = 153.5 mg/kg TPE 4 hours |
| 6 Hz | Single IP drug dose, 6 Hz, 32 mA, 3 seconds, corneal electrode | Mice | $ED_{50}$ = 5.2 mg/kg TPE 4 hours | $ED_{50}$ = 23.4 mg/kg TPE 4 hours |
| 6 Hz | Single IP drug dose, 6 Hz, 22 mA, 3 seconds, corneal electrode | Mice | | "good protection" @ all times @ 100 mg/kg |
| Corn. Kind. | Single IP drug dose, primed @ 8 mA, 60 Hz, 3 secs, for 8 days to bi-daily stage 5 seizures | Mice | $ED_{50}$ = 20.1 mg/kg TPE 4 hours | $ED_{50}$ = 80.4 mg/kg TPE 4 hours |
| Corn. Kind. | Single IP drug dose, primed @ 3 mA, 50 Hz, 3 secs, for 12 days to bi-daily stage 5 seizures | Mice | | $ED_{50}$ = 159 mg/kg |
| scMET | Single IP drug dose, 85 mg/kg | Mice | | Minimal protection up to 1500 mg/kg |
| scMET | 7 days IP, 20 mg/kg dose only, 70 mg/kg | Rat | No protection | 75% protection at 600 mg/kg |
| scPIC | Single IP drug dose, 2.5 mg/kg PIC | Mice | $ED_{50}$ = 60.7 mg/kg TPE 2 hours | Minimal protection up to 100 mg/kg |
| scBIC | Single IP drug dose, 2.7 mg/kg BIC | Mice | About 50% protected from 10-200 mg/kg = inconclusive? | |
| MES | Single IP dose, 50 mA, 2 seconds, corneal electrode | Mice | ED50 = 58.88 mg/kg TPE 6 hours | |

REFERENCES

References Barton M E, Klein B D, Wolf H H and White H S (2001) Pharmacological characterization of the 6 Hz psychomotor seizure model of partial epilepsy. *Epilepsy Res* 47:217-27.

Dunham M S and Miya T A (1957) A note on a simple apparatus for detecting neurological deficit in rats and mice. J. Amer. Pharm. Ass. Sci. Ed 46:208-209.

Swinyard E A, Clark L D, Miyahara J T and Wolf H H (1961) Studies on the mechanism of amphetamine toxicity in aggregated mice. J Physiol 132:97-102.

Swinyard E A, Woodhead J H, White H S and Franklin M R (1989) General principles: experimental selection, quantification, and evaluation of anticonvulsants, in Antiepileptic Drugs (R. H. Levy R H M, B. Melrum, J. K. Penry and F. E. Dreifuss ed) pp 85-102, Raven Press, New York.

Toman J E, Everett G M and Richards R K (1952) The search for new drugs against epilepsy. *Tex Rep Biol Med* 10:96-104.

White H S, Johnson M, Wolf H H and Kupferberg H J (1995a) The early identification of anticonvulsant activity: role of the maximal electroshock and subcutaneous pentylenetetrazol seizure models. ItalJNeurol Sci 16:73-7.

White H S, Woodhead J H and Franklin M R (1995b) General principles: experimental selection, quantification, and evaluation of antiepileptic drugs, in Antiepileptic Drugs (Levy R H M, R. H.; Meldrum, B. S. ed) pp 99-110, Raven Press, New York The disclosure herein is not intended to be limiting and one of skill in the art will recognize that there are other disorders involving GABA that can be treated by the compounds and methods of the present invention.

We claim:

1. A method of reducing collateral damage selected from the group consisting of visual field defects and intramyelinic edema associated with the administration of the gamma-amino butyric acid (GABA) aminotransferase inhibitor vigabatrin to a patient in need thereof, comprising the administration of (1 S,3S)-3-amino-4-difluoromethylenyl-1-cyclopentanoic acid or a salt thereof; wherein the amount administered is from 0.05 to 2.5 mg/kg/day or from about 3.5 to about 175 mg/day for an average adult.

2. The method of claim 1 wherein the patient is addicted to a drug and wherein the (1S,3S)-3-amino-4-difluoromethylenyl-1-cyclopentanoic acid limits dopamine increase after administration of a dopamine agonist to less than about 300% of baseline dopamine levels prior to a challenge with a drug of addiction.

3. The method of claim 2 wherein the amount of (1 S,3S)-3-amino-4-difluoromethylenyl-1-cyclopentanoic acid is from about 1/100 to about 1/700 the dose of vigabatrin.

4. The method of claim 2 wherein the drug is selected from at least one of the following: cocaine, nicotine, methamphetamine, morphine, heroin, ethanol, phencyclidine(PCP), or methylenedioxymethamphetamine.

5. The method of claim 2 wherein the dopamine levels are reduced more than 50% in comparison to an untreated subject.

6. The method of claim 1 wherein the patient suffers from a neurological or psychological disorder.

7. The method of claim 6 wherein the neurological disorder is selected from epilepsy, fibromyalgia, neuropathic pain, migraine related to epilepsy, restless leg syndrome and post traumatic stress disorder addiction, obesity, obsessive-compulsive disorders and Alzheimer's disease.

8. The method of claim 6 wherein the patient suffers from a psychological disorder selected from one or more of the following: general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders.

9. The method of claim 1 wherein the amount of (1 S,3S)-3-amino-4-difluoromethylenyl-1-cyclopentanoic acid is from about 1/100 to about 1/700 the dose of vigabatrin.

10. The method of claim 1 wherein addictive liability is reduced in a patient taking an addictive agent by co-administering (1 S,3S)-3-amino-4-difluoromethylenyl-1-cyclopentanoic acid along with the addictive agent.

11. The method of claim 10, where the (1 S,3S)-3-amino-4-difluoromethylenyl-1-cyclopentanoic acid is administered prior to, concurrently with of after administration of the addictive agent.

12. The method of claim 1 wherein the dose of (1 S,3S)-3-amino-4-difluoromethylenyl-1-cyclopentanoic acid or a salt thereof is 2 to 2.5 mg/kg/day for treatment of epilepsy or about 140-175 mg/day for an average 70 kg adult.

13. The method of claim 1 wherein the dose of (1 S,3S)-3-amino-4-difluoromethylenyl-1-cyclopentanoic acid or a salt thereof is 0.05 to 0.2 mg/kg/day, or about 3.0-15 mg/day for the average 70 kg adult.

14. A method of reducing collateral damage selected from the group consisting of visual field defects and intramyelinic edema associated with the administration of the gamma-amino butyric acid (GABA) aminotransferase inhibitor vigabatrin to a patient in need thereof, comprising the administration of (1 S,3S)-3-amino-4-difluoromethylenyl-1-cyclopentanoic acid or a salt thereof; wherein the amount administered is from 0.05 to 2.5 mg/kg/day or from about 3.5 to about 175 mg/day for an average adult; wherein the (1 S,3S)-3-amino-4-difluoromethylenyl-1-cyclopentanoic acid inactivates GABA aminotransferase through a di-fluoromethylene intermediate instead of 4-oxohex-5-enoic acid.

15. The method of claim 1 wherein the patient suffers from epilepsy.

16. The method of claim 15 wherein the amount of (1 S,3S)-3-amino-4-difluoromethylenyl-1-cyclopentanoic acid is from about 1/100 to about 1/700 the dose of vigabatrin.

17. The method of claim 14 wherein the dose of (1 S,3S)-3-amino-4-difluoromethylenyl-1-cyclopentanoic acid or a salt thereof is 2 to 2.5 mg/kg/day for treatment of epilepsy or about 140-175 mg/day for an average 70 kg adult.

18. The method of claim 14 wherein the dose of (1 S,3S)-3-amino-4-difluoromethylenyl-1-cyclopentanoic acid or a salt thereof is 0.05 to 0.2 mg/kg/day, or about 3.0-15 mg/day for the average 70 kg adult.

19. A method of reducing collateral damage selected from the group consisting of visual field defects and intramyelinic edema associated with the administration of the gamma-amino butyric acid (GABA) aminotransferase inhibitor vigabatrin to a patient in need thereof, comprising the administration of (1 S,3S)-3-amino-4-difluoromethylenyl-1-cyclopentanoic acid or a salt thereof; wherein the amount administered is from 0.05 to 2.5 mg/kg/day or from about 3.5 to about 175 mg/day for an average adult; wherein GABA aminotransferase is inhibited without preventing reuptake of GABA.

20. The method of claim 19 wherein the dose of (1 S,3S)-3-amino-4-difluoromethylenyl-1-cyclopentanoic acid or a salt thereof is 2 to 2.5 mg/kg/day for treatment of epilepsy or about 140-175 mg/day for an average 70 kg adult.

21. The method of claim 19 wherein the dose of (1 S,3S)-3-amino-4-difluoromethylenyl-1-cyclopentanoic acid or a salt thereof is 0.05 to 0.2 mg/kg/day, or about 3.0-15 mg/day for the average 70 kg adult.

* * * * *